(12) United States Patent
Conrath et al.

(10) Patent No.: US 11,759,565 B2
(45) Date of Patent: Sep. 19, 2023

(54) FLOW ADAPTER FOR DRUG DELIVERY DEVICE

(71) Applicant: AMGEN INC., Thousand Oaks, CA (US)

(72) Inventors: Carl Conrath, Thousand Oaks, CA (US); Ali Nekouzadeh, Simi Valley, CA (US); Basel Hasan Taha, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 598 days.

(21) Appl. No.: 16/649,412

(22) PCT Filed: Sep. 26, 2018

(86) PCT No.: PCT/US2018/052810
§ 371 (c)(1),
(2) Date: Mar. 20, 2020

(87) PCT Pub. No.: WO2019/070472
PCT Pub. Date: Apr. 11, 2019

(65) Prior Publication Data
US 2020/0297927 A1    Sep. 24, 2020

Related U.S. Application Data

(60) Provisional application No. 62/567,977, filed on Oct. 4, 2017.

(51) Int. Cl.
| A61M 5/168 | (2006.01) |
| A61M 5/142 | (2006.01) |
| A61M 39/22 | (2006.01) |

(52) U.S. Cl.
CPC .... *A61M 5/16813* (2013.01); *A61M 5/14248* (2013.01); *A61M 39/22* (2013.01); *A61M 2005/14252* (2013.01)

(58) Field of Classification Search
CPC .......... A61M 5/16813; A61M 5/14248; A61M 39/22; A61M 2005/14252; A61M 5/1452; A61M 5/16804
See application file for complete search history.

(56) References Cited

U.S. PATENT DOCUMENTS 4,451,255 A * 5/1984 Bujan ............... A61M 5/16827
604/153
6,186,982 B1    2/2001 Gross et al.
(Continued)

FOREIGN PATENT DOCUMENTS

| WO | WO-03/100356 A1 | 12/2003 |
| WO | WO-2011156373 A1 | 12/2011 |
| WO | WO-2015073604 A1 | 5/2015 |

OTHER PUBLICATIONS

International Search Report for International Application No. PCT/US2018/052810, dated Jan. 7, 2019.
(Continued)

*Primary Examiner* — James D Ponton
(74) *Attorney, Agent, or Firm* — MARSHALL, GERSTEIN & BORUN LLP; Michael P. Furmanek

(57) ABSTRACT

A drug delivery device includes a housing defining a shell, a container, a drive mechanism, a needle assembly having first and second ends, a fluid flow connection, and a flow adapter, each of which is at least partially disposed within the housing. The container has first and second ends and an inner volume to contain a medicament to be administered to a user. The drive mechanism is adapted to exert a force to urge the medicament out the second end of the container. The fluid flow connection is coupled to the second end of the container and the first end of the needle assembly and is adapted to allow the medicament to flow from the container to the needle assembly. The flow adapter includes at least one protrusion for generating a minor head loss to the (Continued)

medicament flowing within the fluid flow connection and helps to reduce variations of injection rates due to variations in drug product viscosities.

11 Claims, 3 Drawing Sheets

(56) References Cited

U.S. PATENT DOCUMENTS

| | | | | |
|---|---|---|---|---|
| 6,416,293 | B1* | 7/2002 | Bouchard | A61M 60/427 |
| | | | | 417/313 |
| 2003/0018304 | A1* | 1/2003 | Sage, Jr. | A61M 5/148 |
| | | | | 604/246 |
| 2005/0150546 | A1* | 7/2005 | Liepold | F16K 15/18 |
| | | | | 137/68.3 |
| 2008/0051714 | A1* | 2/2008 | Moberg | A61M 5/1413 |
| | | | | 604/135 |
| 2008/0262441 | A1 | 10/2008 | Walborn et al. | |
| 2010/0137842 | A1* | 6/2010 | Gibson | A61M 5/16804 |
| | | | | 604/890.1 |
| 2015/0057613 | A1* | 2/2015 | Clemente | A61M 5/14248 |
| | | | | 604/244 |

OTHER PUBLICATIONS

Written Opinion for International Application No. PCT/US2018/052810, dated Jan. 7, 2019.
European Patent Application No. 18786564.7, Communication Pursuant to Article 94(3) EPC, dated Nov. 8, 2021.

* cited by examiner

FLOW ADAPTER FOR DRUG DELIVERY DEVICE

CROSS-REFERENCE TO RELATED APPLICATIONS

Priority is claimed to U.S. Provisional Patent Application No. 62/567,977, filed Oct. 4, 2017, the entire contents of which are expressly incorporated herein by reference.

FIELD OF THE DISCLOSURE

The present disclosure generally relates to drug delivery devices and, more particularly, to drug delivery devices having reduced variance in injection rates.

BACKGROUND

Drug delivery devices, such as injectors, are used to deliver liquid drugs to a patient. Upon activation, a drug delivery device will expel a drug stored within an internal reservoir through a hypodermic needle, cannula, or other delivery member into the patient. Some drug delivery devices, such as on-body injectors, may be temporarily attached to a patient to deliver a drug via a hypodermic needle, cannula or some other means over an extended period of time. The drug delivery device may be adhesively attached to the tissue of the patient's abdomen, thigh, arm, or some other portion of the patient's body.

In some cases, a viscosity of the drug may vary due to a number of factors such as internal and/or external temperatures and drug concentration. The drug's viscosity may vary during a single drug administration process and may also vary among different drug delivery processes. For example, in some environments, the drug may initially have a high viscosity and thus require substantially high forces to maintain flow rates, but upon the drug's viscosity decreasing due to an increase in temperature, for example, lesser forces and higher flow rates may result. In some cases, if the drug's viscosity is different than the viscosity during a previous administration process, a user may become dissatisfied upon experiencing a longer or shorter than expected drug administration, which may lead to patient uncertainty, discomfort, and/or partial dosing due to premature removal of the device by the patient.

SUMMARY

One aspect of the present disclosure provides a drug delivery device that includes a housing defining a shell, a container, a drive mechanism, a needle assembly having first and second ends, a fluid flow connection, and a flow adapter, each of which is at least partially disposed within the housing. The container has first and second ends and an inner volume to contain a medicament to be administered to a user. The drive mechanism is adapted to exert a force to urge the medicament out of the second end of the container. The fluid flow connection is coupled to the second end of the container and the first end of the needle assembly and is adapted to allow the medicament to flow from the container to the needle assembly. The flow adapter includes at least one protrusion for generating a minor head loss to the medicament flowing within the fluid flow connection.

In some examples, the flow adapter includes an elongated member having a shell that defines an inner volume. The inner volume includes at least one protrusion extending inwardly from the shell into the inner volume. In some of these examples, the at least one protrusion may form a narrow channel portion through the inner volume. In other examples, the at least one protrusion may be in the form of an orifice.

In still other forms, the at least one protrusion may be a globe or a gate valve. The globe valve may be manually controlled upon actuating the drug delivery device. Alternatively, the globe valve may be electronically controlled via a controller.

In some approaches, the flow adapter may include any number and combination of narrow channels, orifices, valves, and the like.

In many approaches, the fluid flow connection is constructed from a flexible tube. The flexible tube is constructed from a polymer material. Further, the flow adapter may be constructed from a material having a greater rigidity than the flexible tube such as, for example, a metallic material.

A second aspect of the present disclosure provides a flow adapter for a drug delivery device having a housing, a container at least partially disposed within the housing and adapted to contain a medicament to be administered to a user, a drive mechanism at least partially disposed within the housing, a needle assembly at least partially disposed within the housing, and a fluid flow connection coupled to the container and the needle assembly. The flow adapter includes an elongated member having a shell that defines an inner volume. The inner volume includes at least one protrusion extending inwardly from the shell into the inner volume. The flow adapter is configured to generate a minor head loss to a medicament flowing within the fluid flow connection.

A third aspect of the present disclosure provides a wearable drug delivery device that is securable to a user via an adhesive patch. The wearable drug delivery device includes a housing defining a shell, an activation button coupled to the housing, a container, a drive mechanism, and a needle assembly each being at least partially disposed within the housing, a fluid flow connection, and a flow adapter disposed in line with the fluid flow connection. The container has a first end, a second end, and an inner volume to contain a medicament to be administered to a user upon actuation of the activation button. Upon actuation of the activation button, the drive mechanism is adapted to exert a force to urge the medicament out the second end of the container. The needle assembly has a first end and a second end. The fluid flow connection is coupled to the second end of the container and the first end of the needle assembly. Further, the fluid flow connection is adapted to allow the medicament to flow from the container to the needle assembly. The flow adapter includes an elongated member having a shell that defines an inner volume. The inner volume includes at least one protrusion extending inwardly from the shell into the inner volume for generating a minor head loss to the medicament flowing within the fluid flow connection.

BRIEF DESCRIPTION OF THE DRAWINGS

The above needs are at least partially met through provision of the flow adapter for a drug delivery device described in the following detailed description, particularly when studied in conjunction with the drawings, wherein.

Figure 1:
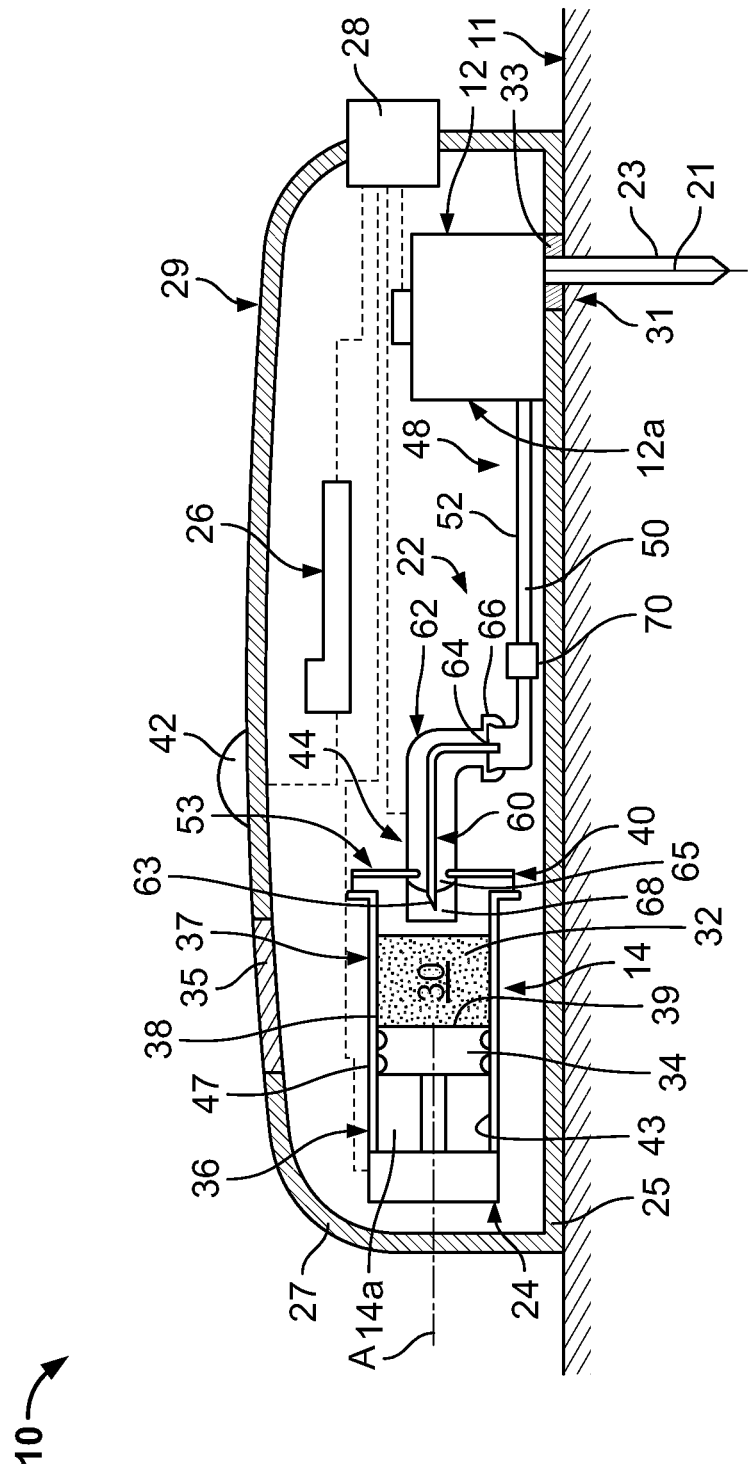
FIG. 1 illustrates a schematic cross-sectional view of an embodiment of a drug delivery device in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a flow adapter for a drug delivery device. Generally, the drug delivery device includes a housing defining a shell, a container, a drive mechanism, a needle assembly having first and second ends, a fluid flow connection, and a flow adapter, each of which is at least partially disposed within the housing. The container has first and second ends and an inner volume to contain a medicament to be administered to a user. The drive mechanism is adapted to exert a force on the first end of the container to urge the medicament through the container towards the second end thereof. The fluid flow connection is coupled to the second end of the container and the first end of the needle assembly and is adapted to allow the medicament to flow from the container to the needle assembly.

The flow adapter is a fluid path element that generates a minor head loss to the medicament flowing within the fluid flow connection. Because the flow adapter is designed as a source of minor head loss, it causes a pressure drop in the fluid flowing across the flow adapter that depends on the flow rate but does not depend explicitly on fluid dynamic viscosity. As a result, the pressure drop over the flow adapter regulates the flow rate by reducing the drive pressure at a factor that is directly proportional to the square of the flow velocity. Further, the flow adapter serves as a reserved pressure which can be accessed in the event of an unexpected increase in resistive pressure of the tissue and/or fluid path to complete the injection at a lower rate. Using a source of minor loss for the flow adaptor (as opposed to a source of major loss) provides the advantage of having less variability in the injection rate of the medicament across a range of viscosities. The resulting minor head loss reduces the sensitivity of injection time to the drug viscosity. As a result, the flow adapter may eliminate the need for expensive electromechanical drive systems and/or closed loop feedback controls and/or systems.

FIG. 1 is a schematic illustration of one embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). In other embodiments (not illustrated), the drug delivery device 10 may be configured as a pen-type injector, such as a handheld autoinjector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include a needle assembly or insertion mechanism 12, a container 14, a fluid pathway assembly 22, a drive mechanism 24, and a controller 26, each of which may be disposed within an interior space of a main housing 29 that defines a shell. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the first end 14a of the stationary container 14, or cause the container 14 to move towards the stationary fluid pathway assembly 22, and thereby cause a container access needle to penetrate through a seal member into a reservoir or interior volume 14a of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a drug 32 contained therein. The one or more visual indicators 42 may be used to communicate information to the user about the operational state of the drug delivery device 10 and/or the condition of the medicament or drug 32. An opening 31 may be formed in the bottom wall 25, and optionally a pierceable sterile barrier 33, such as a pierceable septum, may extend across the opening 31 to seal the interior of the housing 29 prior to use. In some embodiments, the pierceable sterile barrier 33 may be omitted, and instead a removable sealing member (not illustrated) may cover and seal close the opening 31 prior to use.

After the bottom wall 25 of the housing 29 is attached to the patient's tissue 13, the insertion mechanism 12 may be activated to move a delivery member from a retracted position within the housing 29 to a deployed position extending outside of the housing 29. In the present embodiment, this may include the insertion mechanism 12 inserting a needle or trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the needle 21, leaving the distal open end of the cannula 23 inside the patient for subcutaneous delivery of the drug 32. The needle 21 may be solid and have a sharpened end for piercing the patient's skin 11. Furthermore, the needle 21 may be made of a material that is more rigid than the cannula 23. In some embodiments, the needle 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient.

In some embodiments, the insertion mechanism 12 may include one or more springs (e.g., coil springs, torsion springs, etc.) initially retained in an energized state, and which are released upon depression of the actuator 28 in order to insert the needle 21 and cannula 23, or hollow needle, into the patient. Furthermore, retraction of the needle 21 may be achieved by the automatic release of another spring after the needle 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

The container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a first end 36 of the container 14. The stopper 34 may sealingly and slidably engage the interior surface 43 of the wall 38 of the container 14, and may be movable relative to the wall 38 of the container 14.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 30 may be completely or partially filled with the drug 32. The drug 32 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may exert a force on the first end 36 of the container 14. For example, the drive mechanism 24 may push the stopper 34 along the longitudinal axis A from the first end 36 of the container 14 to a second end 37 of the container 14 in order to expel or urge the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A from the proximal end 36 of the container 14 to the second end 37 of the container 14. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy. Other examples are possible.

The fluid pathway assembly 22 may be configured to establish fluid communication between the container 14 and the insertion mechanism 12 via a sterile fluid flow path during operation of the drug delivery device 10. The first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with a fluid flow connection 50.

The fluid pathway assembly 22 may include a first end 44 connected to the second end 37 of the container 14, a second end 48 connected to a first end 12a of the insertion mechanism 12, the fluid flow connection 50 extending between the first end 44 and the second end 48, and a flow adapter 70 disposed within the fluid flow connection 50. As described in more detail below, in some embodiments the first end 44 of the fluid pathway assembly 22 may be connected to the container 14 via a clip member 53. The fluid flow connection 50 may be sterilized, and may be partially or entirely made of a flexible tubing 52 such as, for example, a polymer or other material. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29.

As illustrated in FIGS. 2-6, the flow adapter 70 is an elongated member having a shell 72 that defines an inner volume 73. In some examples, the flow adapter 70 is inserted into the flexible tubing 52 of the fluid flow connection 50. In other examples, the fluid flow connection 50 may be formed in two or more sections, and the flow adapter 70 may be used to connect these sections using any number of approaches. Other examples are possible.

Figure 2:
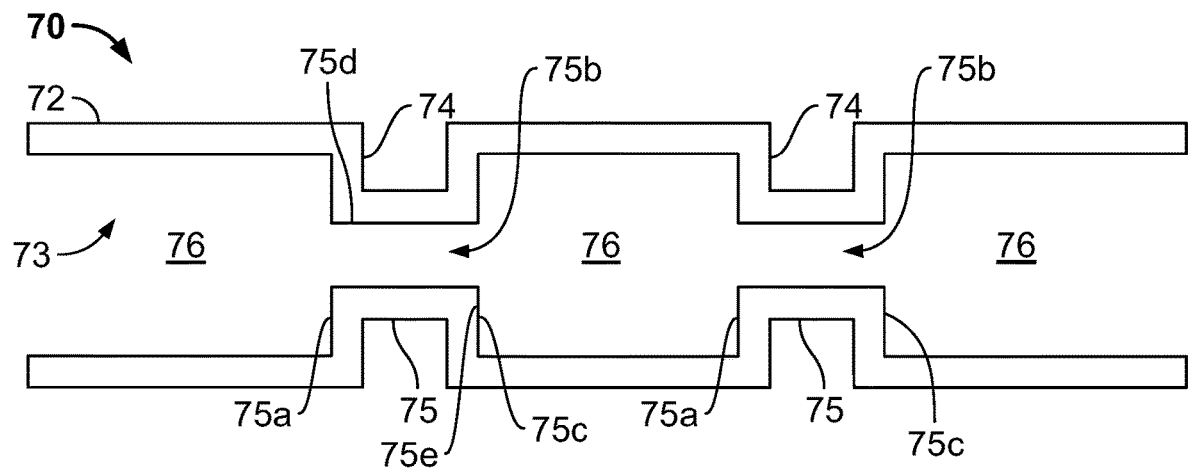
FIG. 2 illustrates a cross-sectional view of an example flow adapter for the drug delivery device of FIG. 1 in accordance with various embodiments.

The inner volume 73 of the flow adapter 70 includes any number of protrusions 74 that extend inwardly into the inner volume 73. For example, as illustrated in FIG. 2, the flow adapter 70 can include any number of protrusions 74 defining narrow channel portions 75 positioned between expanded portions 76. The narrow channel portions 75 restrict flow of the medicament 30. The narrow channel portions 75 can include a front surface 75a, a narrow channel 75b, and a rear surface 75c. The front surface 75a may have any number of orientations to impact flow of the drug 30. For example, and as illustrated in FIG. 2, the front surface 75a may be generally perpendicular to the flow path to create a substantial disruption in fluid flow. In other examples, the front surface 75a may form an oblique angle relative to the fluid flow path.

A corner connection point 75d between the front surface 75a and the narrow channel 75b may be a right angle or may alternatively be a beveled and/or a chamfered edge. Other examples are possible. In some examples, the narrow channel 75b is generally cylindrical in shape and thus may have a generally circular cross section. In other examples, the narrow channel 75b may be tapered (e.g., convergent) such that the opening formed at the front surface 75a is larger than the opening formed at the rear surface 75c. Alternatively, the narrow channel 75b may be tapered (e.g., divergent) such that the opening formed at the front surface 75a is smaller than the opening formed at the rear surface 75c. Other shapes and/or configurations of the narrow channel 75c are possible.

Like the front surface, the rear surface 75c may have any number of orientations to impact flow of the drug 30. For example, and as illustrated in FIG. 2, the rear surface 75c may be generally perpendicular to the flow path. In other examples, the rear surface 75c may form an oblique angle relative to the fluid flow path. A corner connection point 75e between the narrow channel 75b and the rear surface 75c may be a right angle or may alternatively be a beveled and/or a chamfered edge. Other examples are possible.

The narrow channel 75b and the expanded portions 76 may cooperate to cause a sudden expansion in fluid flow, which may in turn create a minor head loss. As a result, the device 10 may produce consistent and predictable injection rates when delivering the drug 32.

Figure 3:
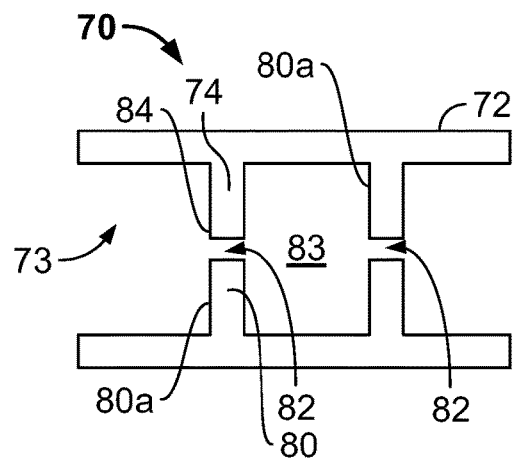
FIG. 3 illustrates a cross-sectional view of an alternative example flow adapter for the drug delivery device of FIG. 1 in accordance with various embodiments.

In other examples, and as illustrated in FIG. 3, the flow adapter 70 can include any number of protrusions 74 in the form of walls 80 that include any number of orifices 82. The flow adapter 70, and any number of the components thereof, can be constructed from a material having a greater rigidity than the flexible tube 52. For example, the flow adapter 70 may be constructed from a metallic material, a plastic or a polymer, a glass, and/or a ceramic material. The flow adapter 70 may be constructed from a single material or a combination of mixed material types. In some examples, the walls 80 may be separated by an open area 83 defined by the shell 72. A front surface 80a may have any number of orientations to impact flow of the drug 30. For example, and as illustrated in FIG. 3, the front surface 80a may be generally perpendicular to the flow path to create a substantial disruption in fluid flow. In other examples, the front surface 80a may form an oblique angle relative to the fluid flow path.

The orifices 82 may be of any size, shape, and/or orientation relative to the walls 80. For example, and as illustrated in FIG. 3, the orifices 82 may be formed at a perpendicular angle relative to the walls 80. In other examples, the orifices 82 may be formed at non-perpendicular angles relative to the walls 80. An edge 84 formed by the walls 80 and the orifices 82 may be beveled, rounded, chamfered, and/or perpendicular to affect flow of the drug 30. Other examples are possible.

Figure 4:
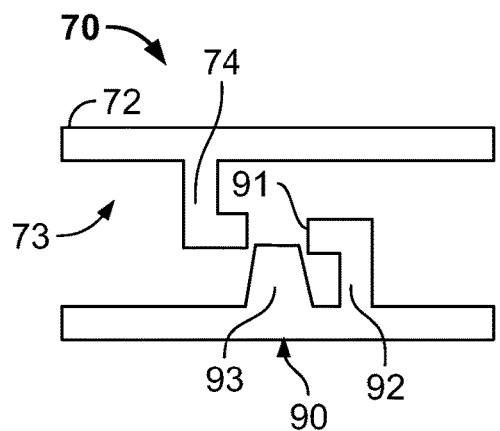
FIG. 4 illustrates a cross-sectional view of another alternative example flow adapter for the drug delivery device of FIG. 1 in accordance with various embodiments.

In other examples, and as illustrated in FIG. 4, the flow adapter 70 can include any number of protrusions 74 in an arrangement of a globe valve 90. The globe valve 90 may include a seating portion 91 extending from a plurality of inwardly-protruding walls 92 and a plug 93. In some examples, the plug 93 is movable to engage the seating portion 91, thereby limiting and/or restricting fluid flow. In other examples, the plug 93 may be stationary, and the walls 92 and/or the seating portion 91 may movably engage the plug 93. In still other examples, the seating portion 91, the walls 92, and the plug 93 may remain stationary and thus affect fluid flow by altering the flow path of the drug 30.

In examples where the seating portion 91, the walls 92, and/or the plug 93 are movable, the moving component may be manually controlled upon actuating the actuator 28. In other words, the actuator 28 may include a mechanical coupling that extends to the flow adaptor 70 that causes the seating portion 91, the walls 92, and/or the plug 93 to move. In other examples, movement of the seating portion 91, the walls 92, and/or the plug 93 may be electronically controlled via any number of computing systems or other components. Other examples are possible. In some examples, the opening formed between the plug 93 and the seating portion 91 may be adjusted to achieve a desired flow restriction.

Figure 5:
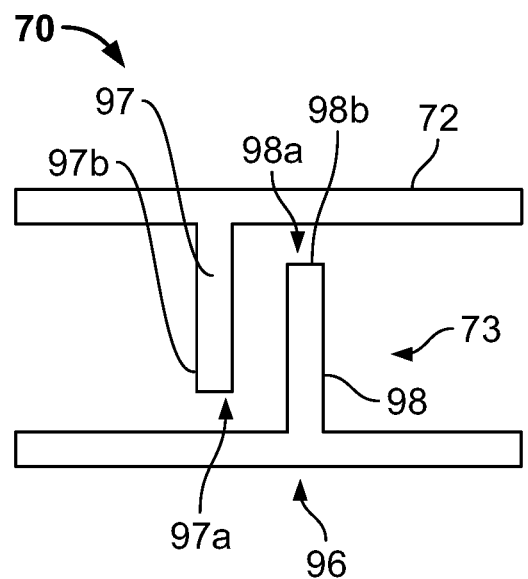
FIG. 5 illustrates a cross-sectional view of yet another alternative example flow adapter for the drug delivery device of FIG. 1 in accordance with various embodiments.

In other examples, and as illustrated in FIG. 5, the flow adapter 70 can include any number of protrusions 74 in an arrangement of a gate valve 96. The gate valve 96 may include any number of walls 97, 98 disposed in the interior volume 73 of the shell 72. The walls 78, 79 extend partially into the interior volume 73 such that an opening 97a, 98b is formed between the ends 97b, 98b of the walls 97, 98, respectively, and the opposite side of the shell 72 from which the walls 97, 98 extend. In some examples, the ends 97b, 98b of the walls 97, 98 are generally flat and extend in a direction that is parallel to the fluid flow path. In other examples, the ends 97b, 98b of the walls 97, 98 may have any other suitable configuration. Further, while the example illustrated in FIG. 5 includes two walls 97, 98, the gate valve 96 may have any number of walls that protrude into the interior volume 73 of the shell 72.

In some examples, any number of the walls 97, 98 are movable to further extend into the interior volume 73 to engage the opposite side of the shell 72, thereby limiting and/or restricting fluid flow. In other examples, the walls 97, 98 may be stationary, and the shell 72 may be movable or compressible to reduce an overall diameter or dimension of the interior volume 73 such that the walls 97, 98 engage the opposite side of the shell 72. In still other examples, the walls 97, 98 and the shell may remain stationary and thus affect fluid flow by altering the flow path of the drug 30.

In examples where the walls 97, 98 and/or the shell 72 are movable, the moving component may be manually controlled upon actuating the actuator 28. In other words, the actuator 28 may include a mechanical coupling that extends to the flow adaptor 70 that causes the walls 97, 98 and/or the shell 72 to move. In other examples, movement of the walls 97, 98 and/or the shell 72 may be electronically controlled via any number of computing systems or other components. Other examples are possible. In some examples, a size of the opening 97a, 98a formed between the walls and the shell 72 may be adjusted to achieve a desired flow restriction.

Figure 6:
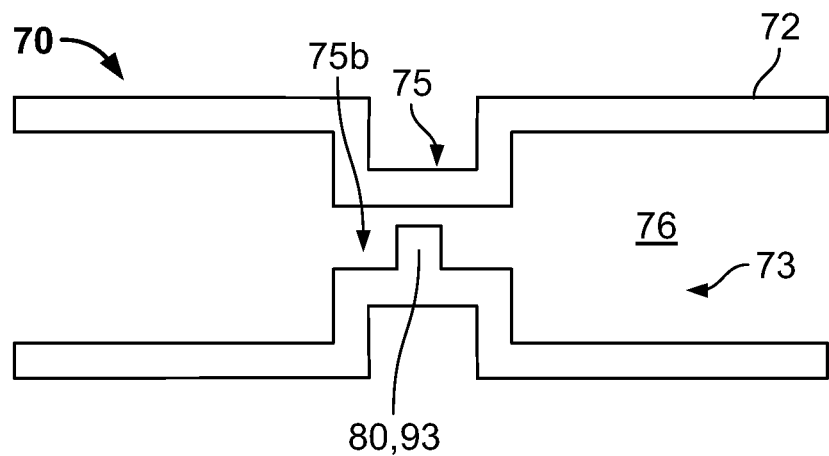
FIG. 6 illustrates a cross-sectional view of a further alternative example flow adapter for the drug delivery device of FIG. 1 in accordance with various embodiments.

In other examples, and as illustrated in FIG. 6, the flow adapter 70 can include any number of previously-described protrusions 74 used in conjunction with each other. For example, a narrow channel portion 75 may be formed that includes an additional wall 80 and/or a plug 93 positioned in the narrow channel 75b. Any or all of these components may be movable relative to the shell 72 to create a desired flow reduction.

So configured, the flow adapter 70 generates an optimal amount of minor head loss to reduce the variability in fluid injection rates. The flow adapter 70 may be beneficial in limiting changes to injection rates caused by changes of the drug's viscosity. The flow adapter 70 may further enable reducing major loss, or pressure drops that occur due to fluid friction without increasing the injection rate. By providing the flow adaptor 70, major losses are reduced, thereby reducing the required forces to drive the drug 30 at the same injection rate at higher than nominal viscosities. Further, in examples where the injector is in the form of a pen-type or handheld injector, reduced variability of flow rates can reduce occurrences of the patient misjudging injection times and prematurely removing the device. Additionally, the flow adapter 70 can be implemented in handheld devices in a cost-effective manner, since these devices may not contain complex electromechanical drive systems with feedback to correct variability.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

Drug Information

As mentioned above, the container of the drug delivery device may be filled with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamoylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosumab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD;

AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody*7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA ($\gamma$4), deposited at the ATCC under number PTA-5214, and a light chain encoded by a polynucleotide in plasmid 15H12/19D12 LCF ($\kappa$), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath®

(alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4 integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A drug delivery device comprising:
    a housing defining a shell;
    a container at least partially disposed within the housing, the container having a first end and a second end and an inner volume adapted to contain a medicament to be administered to a user;
    a drive mechanism at least partially disposed within the housing, the drive mechanism adapted to exert a force to urge the medicament out the second end of the container at a specified injection rate;
    a needle assembly at least partially disposed within the housing, the needle assembly having a first end and a second end;
    a fluid flow connection coupled to the second end of the container and the first end of the needle assembly, the fluid flow connection adapted to allow the medicament to flow from the container to the needle assembly; and
    a flow adapter disposed in line with the fluid flow connection, the flow adapter comprising an elongated member having a rigid shell that defines an inner volume including at least one protrusion extending inwardly from the rigid shell into the inner volume thereof, the at least one protrusion adapted to affect flow of the medicament to generate a minor head loss to the medicament flowing within the fluid flow connection, thereby regulating a flow rate of the medicament while reducing variability between the flow rate and the specified injection rate, wherein the rigid shell is constructed from a material having a greater rigidity than the fluid flow connection.

2. The drug delivery device of claim 1, wherein the at least one protrusion forms a narrow channel portion through the inner volume.

3. The drug delivery device of claim 1, wherein the at least one protrusion comprises an orifice.

4. The drug delivery device of claim 1, wherein the at least one protrusion comprises a globe valve.

5. The drug delivery device of claim 4, wherein the globe valve is manually controlled upon actuating the drug delivery device or electronically controlled via a controller.

6. The drug delivery device of claim 1, wherein the at least one protrusion comprises a gate valve.

7. The drug delivery device of claim 1, wherein the at least one protrusion comprises at least one of:
   a narrow channel portion;
   an orifice;
   a globe valve; or
   a gate valve.

8. The drug delivery device of claim 1, wherein the fluid flow connection is constructed from a flexible tube.

9. The drug delivery device of claim 8, wherein the flexible tube is constructed from a polymer material.

10. The drug delivery device of claim 1, wherein the flow adapter is constructed from a metallic material.

11. A wearable drug delivery device adapted to be secured to a user via an adhesive patch, the wearable drug delivery device comprising:
   a housing defining a shell;
   an activation button coupled to the housing;
   a container at least partially disposed within the housing, the container having a first end, a second end, and an inner volume adapted to contain a medicament to be administered to a user upon actuation of the activation button;
   a drive mechanism at least partially disposed within the housing, the drive mechanism, upon actuation of the activation button, adapted to exert a force to urge the medicament out the second end of the container at a specified injection rate;
   a needle assembly at least partially disposed within the housing, the needle assembly having a first end and a second end;
   a fluid flow connection coupled to the second end of the container and the first end of the needle assembly, the fluid flow connection adapted to allow the medicament to flow from the container to the needle assembly; and
   a flow adapter disposed in line with the fluid flow connection, the flow adapter comprising an elongated member having a shell that defines an inner volume, wherein the inner volume of the shell of the flow adapter includes at least one protrusion extending inwardly therefrom into the inner volume thereof, the at least one protrusion configured to affect flow of the drug to generate a minor head loss to the medicament flowing within the fluid flow connection, thereby regulating a flow rate of the medicament while reducing variability between the flow rate and the specified injection rate, wherein the shell of the flow adapter is constructed from a material having a greater rigidity than the fluid flow connection.

* * * * *